(12) United States Patent
Anders

(10) Patent No.: US 8,267,856 B2
(45) Date of Patent: Sep. 18, 2012

(54) LARYNGOSCOPE SPATULA

(75) Inventor: Fridolin Anders, Immendingen-Zimmern (DE)

(73) Assignee: Karl Storz GmbH & Co. KG (DE)

( * ) Notice: Subject to any disclaimer, the term of this patent is extended or adjusted under 35 U.S.C. 154(b) by 345 days.

(21) Appl. No.: 12/535,759

(22) Filed: Aug. 5, 2009

(65) Prior Publication Data

US 2010/0036204 A1   Feb. 11, 2010

(30) Foreign Application Priority Data

Aug. 5, 2008 (DE) .................. 10 2008 036 826

(51) Int. Cl.
*A61B 1/267* (2006.01)
*B21D 39/03* (2006.01)
(52) U.S. Cl. .......................... 600/190; 29/428
(58) Field of Classification Search .......... 600/185–198, 600/210
See application file for complete search history.

(56) References Cited

U.S. PATENT DOCUMENTS

| | | | | |
|---|---|---|---|---|
| 3,426,749 | A * | 2/1969 | Jephcott | 600/186 |
| 3,598,113 | A | 8/1971 | Moore et al. | |
| 4,047,693 | A * | 9/1977 | Holme | 249/187.1 |
| 4,556,052 | A | 12/1985 | Müller | |
| 4,579,108 | A * | 4/1986 | Bauman | 600/186 |
| D631,158 | S * | 1/2011 | Doerges | D24/137 |
| 2003/0032864 | A1* | 2/2003 | Friesen | 600/194 |
| 2006/0079734 | A1 | 4/2006 | Miyagi | |
| 2007/0129607 | A1* | 6/2007 | Ashfaque | 600/194 |
| 2009/0099421 | A1* | 4/2009 | Shalman et al. | 600/197 |
| 2009/0318767 | A1* | 12/2009 | Tenger et al. | 600/194 |

FOREIGN PATENT DOCUMENTS

| | | |
|---|---|---|
| CA | 1183049 A | 2/1985 |
| DE | 1937817 A1 | 4/1970 |
| DE | 1766713 B1 | 1/1971 |
| DE | 2621232 A1 | 11/1977 |
| DE | 3119725 A1 | 12/1982 |
| DE | 3317831 A1 | 11/1984 |
| DE | 20004324 U1 | 7/2000 |
| GB | 2102294 A | 2/1983 |

OTHER PUBLICATIONS

European Search Report; Application No. EP 09 16 6358; Aug. 5, 2010; 4 pages.

* cited by examiner

*Primary Examiner* — Eduardo C Robert
*Assistant Examiner* — Jacqueline Johanas
(74) *Attorney, Agent, or Firm* — St. Onge Steward Johnston & Reens LLC

(57) ABSTRACT

The invention relates to a laryngoscope spatula with a spatula blade. The spatula blade, in cross section, has two side walls, which are spaced apart from each other along at least part of the length of the spatula blade, and two limbs. A first limb extends from the first side wall to beyond the second side wall, and a second limb extends from the second side wall to beyond the first side wall. The side walls and the limbs thus form a cavity. The spatula blade is composed of an upper shell and a lower shell which, in cross section, each have a first portion and two mutually oppositely directed second and third portions. The second portions of the upper shell and lower shell, lying flat on each other, form the first limb, and the third portions, lying flat on each other, form the second limb, while the first portions form the side walls. The invention further relates to a method for producing a spatula blade of such a laryngoscope spatula.

23 Claims, 3 Drawing Sheets

LARYNGOSCOPE SPATULA

CROSS REFERENCE TO FOREIGN APPLICATION

The present application claims priority of German patent application No. 10 2008 036 826.1 filed on Aug. 5, 2008.

BACKGROUND OF THE INVENTION

The invention generally relates to laryngoscope spatulas.

More specifically, the invention relates to a laryngoscope spatula of the kind comprising a spatula blade, which spatula blade, in cross section, has two side walls, which are spaced apart from each other along at least part of the length of the spatula blade, and two limbs, of which a first limb extends from the first side wall to beyond the second side wall, and a second limb extends from the second side wall to beyond the first side wall, the side walls and the limbs forming a cavity.

The invention further relates to a method for producing a spatula blade of a laryngoscope blade.

Such a laryngoscope spatula is arranged on a handle and is used in laryngoscopy and, in particular, in endotracheal intubation. For the latter purpose in particular, the laryngoscope spatula has, in cross section, a profile with a stepped structure which, for example, provides a guide for an endotracheal tube used in intubation. Moreover, in the distal area of the laryngoscope spatula there is arranged a light source or a light outlet end of a light guide, in order to allow the operator to view the larynx.

Whereas these light sources were formerly direct light sources arranged directly on the relevant end, e.g. light bulbs, it is nowadays preferable to use light guides, e.g. glass fibres, by which a light generated by a light source located in the handle area is guided through the laryngoscope spatula to the distal position, from which the light can then emerge.

For arranging the light guide on the laryngoscope spatula, the latter comprises the abovementioned cavity, in which the light guide is protected.

However, in a laryngoscope spatula according to the invention, the aforementioned light guide can serve not only to deliver light from the proximal end to the distal end, so as to irradiate light into the pharynx, but can also be used the other way round to convey light from the pharynx for imaging purposes, i.e. light can enter the light guide at the distal end of the light guide and be conveyed in the proximal direction.

Moreover, in a laryngoscope spatula according to the invention, the cavity can be used to receive electrical leads in a protected manner, which leads are used, for example, to supply voltage to a light source, for example an LED, arranged in the distal area of the laryngoscope spatula, and/or an electronic imager can be arranged in the distal area of the laryngoscope spatula, in which case the cavity then accommodates electrical leads via which the electronic imager is supplied with voltage or via which signals are guided in the proximal direction from the electronic imager to the handle.

In a laryngoscope known from DE 31 19 725 C2, the spatula blade structure mentioned at the outset is achieved by two elongate profiles of L-shaped cross section being fitted on each other to form the cavity. The two L-shaped elongate profiles are offset in cross section by 180 degrees relative to each other. One end of a limb of the first L-shaped profile abuts against a limb of the second L-shaped profile, and the end of the other limb of the second L-shaped profile abuts against the other limb of the first L-shaped profile. The two L-shaped profiles are soldered onto each other at these abutment edges.

A laryngoscope known from DE 33 17 831 C2 has a spatula blade composed of a profile part of Z-shaped cross section and of a profile part of L-shaped cross section, so as to form the cavity. The L-shaped profile part is placed with the free ends of its two limbs along abutment edges onto the Z-shaped profile and is welded onto the Z-shaped profile along the abutment edges. The weld seams are then smoothed by fine grinding and fine polishing.

To ensure that a laryngoscope spatula, as has been described above, can be used several times, it is necessary for it to be able to be thoroughly cleaned and sterilized, for which reason it should not have any recesses, corners or edges where bacteria or other material can settle. It is also necessary to avoid liquids and/or bacteria penetrating into the interior of the spatula blade, since here too it would be possible for bacteria to grow unimpeded.

For this purpose, in the known laryngoscope spatulas described above, it is necessary for the two profile parts to be welded or soldered onto each other in a leaktight manner, and for these solders or welds to be reworked so as to produce a smooth surface. This is in most cases followed by a galvanization step in order to ensure an optimally smooth surface and to avoid any material irregularities that would make subsequent cleaning difficult. The known laryngoscopes spatulas are therefore expensive to make, and the production of the known laryngoscope spatulas is also complicated.

SUMMARY OF THE INVENTION

It is therefore an object of the present invention to develop a laryngoscope spatula which is easy to clean but whose production requires the least possible reworking and is therefore relatively simple.

It is also an object of the present invention to make available a method for producing a spatula blade for such a laryngoscope spatula.

According to a first aspect of the invention, a laryngoscope spatula comprises:
a spatula blade having a length in a longitudinal direction, the spatula blade having:
an upper shell having, in cross-section transverse to the longitudinal direction, a first upper shell portion, a second upper shell portion and a third upper shell portion, the second upper shell portion and the third upper shell portion being mutually oppositely directed away from the first upper shell portion; a lower shell having, in cross-section transverse to the longitudinal direction, a first lower shell portion, a second lower shell portion and a third lower shell portion, the second lower shell portion and the third lower shell portion being mutually oppositely directed away from the first lower shell portion; the first upper shell portion forming a first side wall and the first lower shell portion forming a second side wall spaced apart from the first side wall along at least part of the length of the spatula blade; the second upper shell portion and the second lower shell portion partially lying flat on each other and forming a first limb extending from the first side wall to beyond the second side wall; the third upper shell portion and the third lower shell portion partially lying flat on each other and forming a second limb extending from the second side wall to beyond the first side wall; the first and second side walls and the first and second limbs forming a cavity.

According to another aspect of the invention, a method for producing a spatula blade of a laryngoscope spatula comprises the steps of:
providing an upper shell and a lower shell, wherein the upper shell, in cross-section transverse to a longitudinal direction, has a first upper shell portion, a second upper shell portion and a third upper shell portion, the second upper shell portion and the third upper shell portion being mutually oppositely directed away from the first upper shell portion, the lower shell having, in cross-section transverse to the longitudinal direction, a first lower shell portion, a second lower shell portion and a third lower shell portion, the second lower shell portion and the third lower shell portion being mutually oppositely directed away from the first lower shell portion, laying the second upper shell portion flat on the second lower shell portion, and laying the third upper shell portion flat on the third lower shell portion, firmly connecting the upper shell and the lower shell to each other by joining the second upper and lower shell portions and the third upper shell and lower shell portions such that the second upper and lower shell portions form a first limb and the third upper and lower shell portions form a second limb, and the first upper shell portion forms a first side wall and the first lower shell portion forms a second side wall, as a result of which a cavity is formed along at least part of a length of the spatula blade.

The laryngoscope spatula according to the invention thus comprises a spatula blade formed by joining together an tipper shell and a lower shell which both, in cross section, have a substantially Z-shaped profile. The substantially Z-shaped upper shell and the substantially Z-shaped lower shell are laterally offset relative to each other, with the same orientation of the "Z", such that the second and third portions of the upper shell and lower shell lie flat on each other, while the first portions, i.e. the middle limbs of the Z-shaped profiles, form the mutually spaced apart side walls of the spatula blade. By laying the second and third portions of the upper shell and lower shall flat on each other, abutment edges of the kind found in the prior art are avoided, which abutment edges are difficult to join by soldering or welding and, in particular, require extensive reworking in order to achieve a smooth surface. In the laryngoscope spatula according to the invention, the upper shell and lower shell each form the complete surface of the spatula blade. This has the effect that the surface of the spatula blade, on its top side and underside, is free from weld seams that require reworking. Compared to the known laryngoscope spatulas, the laryngoscope spatula according to the invention can be produced with fewer working steps, which also reduces the design costs of the laryngoscope spatula according to the invention.

The production method according to the invention is easy to carry out and, because of the upper shell and lower shell being laid flat on each other via the second and third portions, does not require complicated reworking of weld seams along abutment edges.

In a preferred embodiment of the invention, the cavity is closed off at the distal end by an end wall that extends transversely with respect to the longitudinal direction of the spatula blade, and the end wall is designed in one piece with the first portion and the second portion of the upper shell.

The end wall has the effect that the cavity is closed at the distal end and, for this reason, no fluids etc. can get into it from the distal direction.

A one-piece design with the first and second portions of the upper shell eliminates the need for subsequent formation of such an end wall, as a result of which there is also no need for reworking of the resulting connection points, since a continuous surface without irregularities is obtained from the outset.

In the end wall there is preferably at least one opening for preferably leaktight accommodation of a distal light outlet end and/or light input end of a light guide for illuminating and/or imaging, for accommodating a light source, for example an LED, and/or for accommodating an electronic imager.

In other preferred embodiments of the invention, the lower shell is produced by a forming method, preferably by hydroforming, in which the first portion is formed in one piece with the second and third portions, and/or the upper shell is produced by a forming method, preferably by hydroforming, in which the first portion is formed in one piece with the second and third portions and with the end wall.

These measures have the advantage that the upper shell and lower shell can be produced from one workpiece, for which reason they each have an inherently closed surface. This results in continuous smooth surfaces that are easy to clean. Hydroforming is also particularly suitable for producing the desired three-dimensional geometric shape of the upper shell and lower shell.

Production is also made simpler by the upper shell and/or lower shell each being formed from just one part, which results in savings in terms of time and costs.

In another preferred embodiment of the invention, the upper shell and the lower shell are glued to each other via the superposed second and third portions.

Gluing of the superposed surfaces of the second and third portions of the upper shell and lower shell has the advantage of being able to be done simply, quickly and inexpensively. Moreover, because of the planar connection, this joining technique provides a secure hold of the upper shell and lower shell on each other. In addition, the outer face of the spatula blade is in this case completely free of joints.

In another preferred embodiment of the invention, the upper shell and the lower shell are soldered onto each other along a peripheral contact edge formed by mutually adjoining edges of the second and third portions.

By means of the soldering at the contact edge, a connection is produced only at the outer peripheral area and can be reworked relatively easily and quickly. In this way there is only a connecting seam between upper shell and lower shell, which reduces to a minimum the possibility of bacterial colonization and the penetration of liquids. Moreover, the production method, with only one production step for connecting the shells, takes considerably less time.

In another preferred embodiment of the invention, the upper shell and the lower shell are welded onto each other, preferably by laser welding, along a peripheral contact edge formed by mutually adjoining edges of the second and third portions.

Here too, the welded area can, if appropriate, be easily reworked, although this is not in fact necessary in the particular case of laser welding, since laser welding provides a very smooth connection site, which does not require any further working. This method therefore saves time and money.

In another preferred embodiment of the invention, the spatula blade has a rounded spatula tip at the distal end.

A rounded spatula tip has the advantage of reducing to a minimum the risk of injury when inserting the laryngoscope spatula through the oral cavity in the direction of the larynx.

In another embodiment of the invention, the spatula tip is welded, soldered or glued onto the spatula blade.

This has the advantage that the subsequently attached spatula tip is secured firmly on the distal end of the spatula blade and thus has the required hold during the corresponding interventions. This method means that the spatula tip can be secured in just one additional simple step.

In an alternative preferred embodiment of the invention, the spatula tip is formed in one piece with the upper shell and/or the lower shell.

This design approach has the advantage that the spatula tip does not have to be attached subsequently to the spatula blade and, therefore, an additional production step is eliminated, which improves the overall method of production and makes it quicker.

Further advantages and features will become clear from the following description and from the attached drawing.

It will be appreciated that the aforementioned features and those still to be explained below can be used not only in the respectively cited combination but also in other combinations or singly, without departing from the scope of the present invention.

BRIEF DESCRIPTION OF THE DRAWINGS

The invention is described and explained in more detail below on the basis of a selected illustrative embodiment and with reference to the attached drawings, in which.

DETAILED DESCRIPTION OF A PREFERRED EXEMPLARY EMBODIMENT

Figure 1:
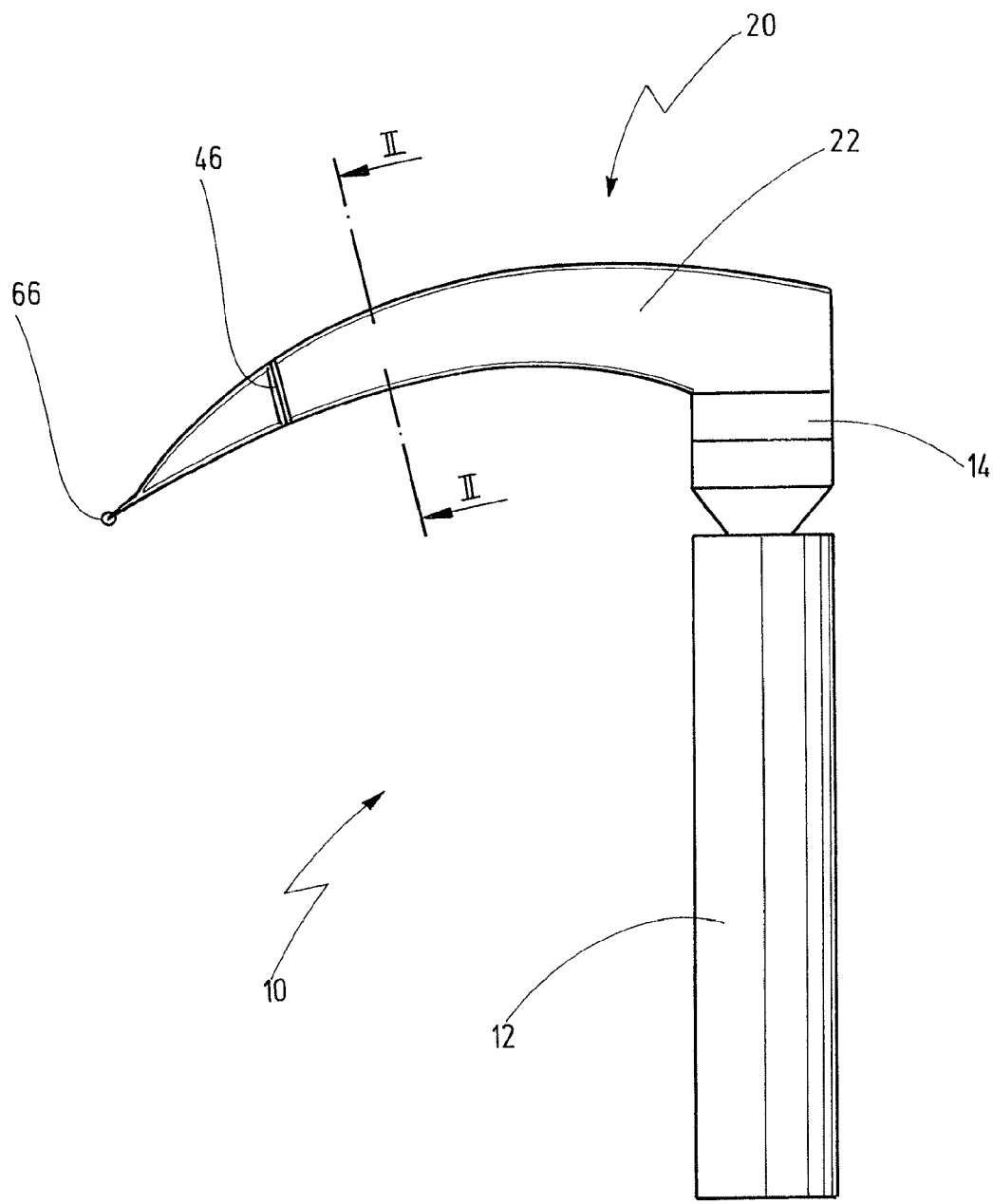
FIG. 1 shows a side view of a laryngoscope.

In FIG. 1, a laryngoscope is designated in its entirety by the general reference sign 10.

The laryngoscope 10 is composed of a handle 12, a head 14 and a laryngoscope spatula 20.

Figure 2:
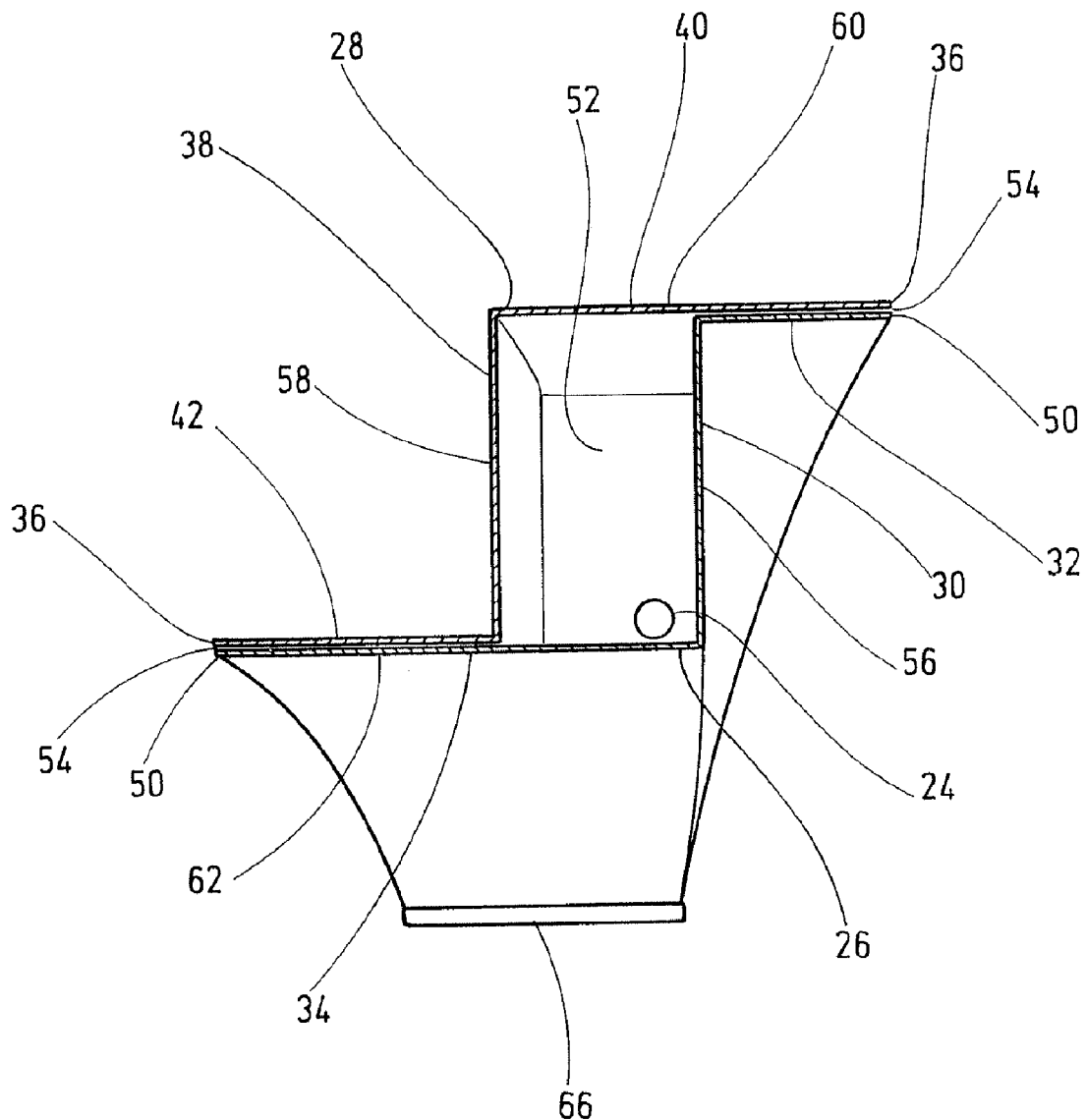
FIG. 2 shows a section along the line II-II in FIG. 1.
Figure 3:
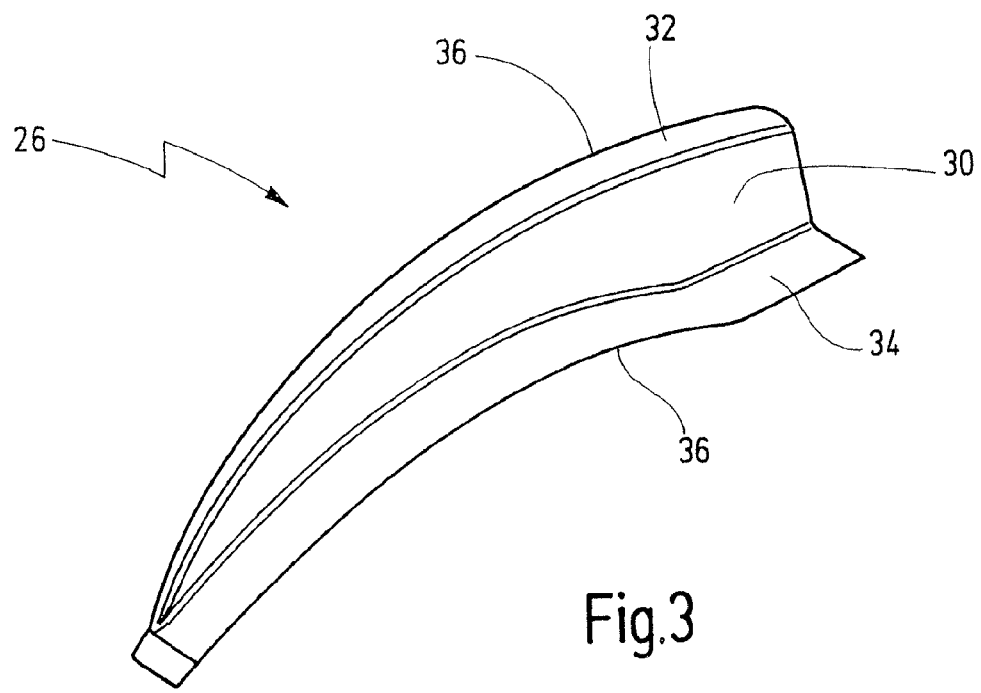
FIG. 3 shows a perspective view of a lower shell, which is part of a spatula blade of the laryngoscope in FIG. 1.
Figure 4:
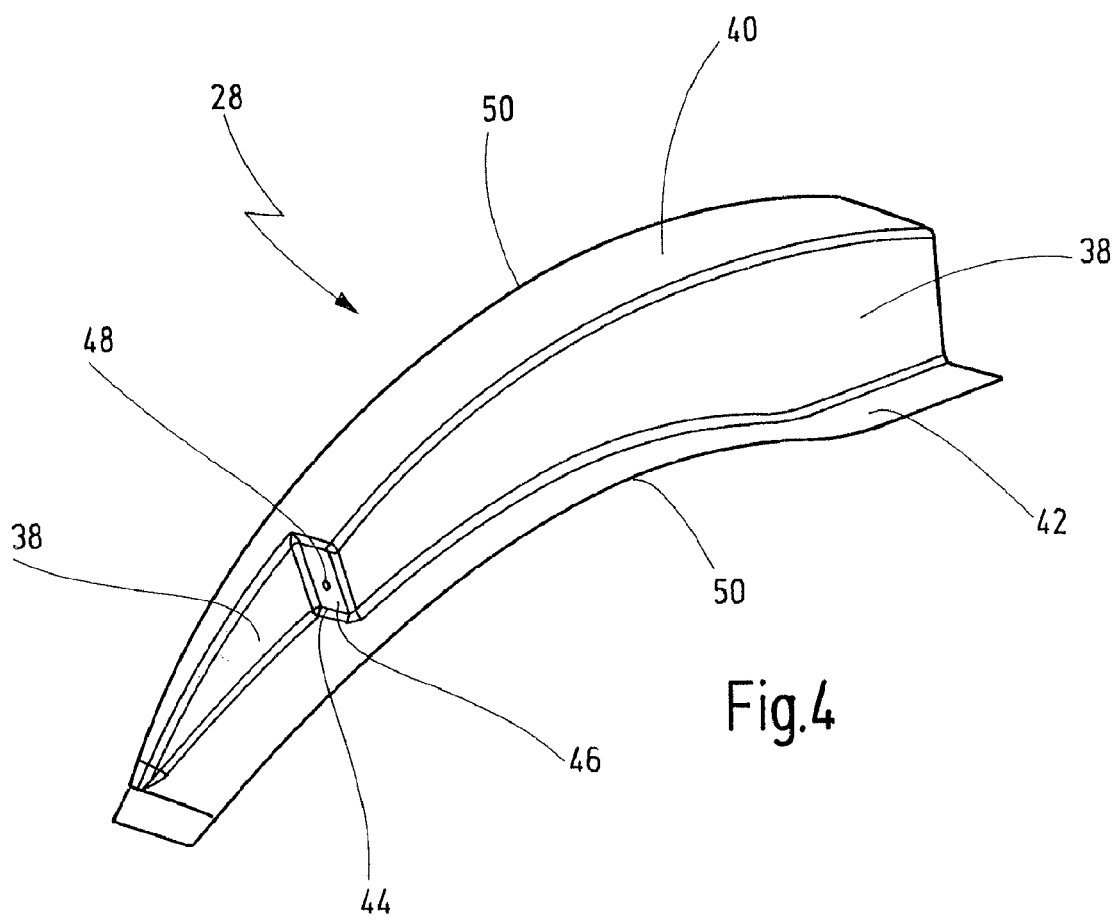
FIG. 4 shows a perspective side view of an upper shell, which is also part of the spatula blade of the laryngoscope in FIG. 1.

Details of the laryngoscope spatula 20 are shown in FIGS. 2 to 4.

The laryngoscope spatula 20 has a spatula blade 22 and, arranged therein, a light guide 24 (FIG. 2). This laryngoscope spatula 20 is connected to a head 14 (shown schematically here), which is then in turn connected to the handle 12.

Instead of or in addition to the light guide 24, one or more electrical leads can extend through the spatula blade 22 to supply voltage to one or more light sources, for example LEDs, in the distal area of the spatula blade 22 or to act as signal line(s) for an electronic imager arranged in the distal area.

The spatula blade 22 shown here has a curved shape adapted to the anatomical conditions of the oropharyngeal cavity of a patient and is composed of a lower shell 26 and an upper shell 28 (FIG. 3 and FIG. 4).

The lower shell 26 is composed of a first portion 30, and of second and third portions 32 and 34 which each extend in opposite directions from a respective end of the first portion 30, and transversely thereto. The portions 32 and 34 are here substantially perpendicular to the portion 30, but they can also be oblique with respect thereto.

Seen in cross section, this results substantially in a Z-shaped profile, in which the substantially horizontal areas of the Z are formed by the second and third portions 32 and 34, and the central limb connecting them is formed by the first portion 30.

The lower shell 26 furthermore comprises a peripheral edge 36 that forms the outer margins of the first, second and third portions 30, 32 and 34 (FIG. 3).

The upper shell 28 seen in FIG. 4 comprises a first portion 38, from the respective ends of which second and third portions 40 and 42 extend in mutually opposite directions and transversely thereto, i.e. perpendicularly, as is shown here, or obliquely with respect to the first portion 38. An end wall 46 is formed by a lateral offset 44 of the first portion 38 in the longitudinal direction of the upper shell 28.

The end wall 46 faces in the distal direction and has an outlet opening 48 in which the light guide 24 is arranged, such that light passing through the light guide 24 can emerge through the outlet opening 48.

When the laryngoscope 10 is in use, it is thus possible to illuminate the oropharyngeal space, as is necessary in laryngoscopy or also in intubation.

Instead of delivering light, the light guide 24 can also serve as an image conductor, for which purpose light can pass into the light guide 24 into the distal end of the light guide 24 located in the outlet opening 48. It is also possible for one or more light sources, for example LEDs, or an electronic imager to be arranged in the outlet opening 48 or in one or more further outlet openings.

In cross section, the upper shell 28 also has a substantially Z-shaped profile formed by the second portion 40, the first portion 38 and the third portion 42.

The upper shell 28 also has a peripheral edge 50, which forms the outer margins of the first, second and third portions 38, 40 and 42.

As will be seen from FIG. 2, the lower shell 26 and the upper shell 28 lie on each other such that a cavity 52 is formed.

For this purpose, the third portion 42 of the upper shell 28 is arranged lying flat on the third portion 34 of the lower shell 26, and the second portion 40 of the upper shell 28 is arranged lying flat on the second portion 32 of the lower shell 26. The peripheral edges 36 and 50 come to lie over each other, such that they form a contact edge 54.

Since the third portion 42 of the upper shell 28 is shorter than the third portion 34 of the lower shell 26 and the second portion 32 of the lower shell 26 is shorter than the second portion 40 of the upper shell 28, the first portions 30 and 38 of the lower shell 26 and of the upper shell 28 are spaced apart from each other, as a result of which the cavity 52 is formed.

The first portions 30 and 38 thus form side walls 56 and 58 of the cavity 52.

Laying the second portions 32 and 40 on each other and the third portions 34 and 42 on each other results in the formation of limbs 60 and 62 of the spatula blade 22. These limbs 60 and 62 form together with the side walls 56 and 58 the boundary of the cavity 52.

The light guide 24, starting from a light source in the handle 12, for example, extends through the cavity 52 as far as the aforementioned outlet opening 48. In the abovementioned cases where, instead of the light guide 24 or in addition to it, one or more light sources, for example LEDs, or an electronic imager are arranged in the distal area of the spatula blade 22, one or more electrical leads run through the cavity 52 to provide voltage to the light source(s) or electronic imager and to act as signal lines for the electrical imager.

In the illustrative embodiment shown here, the upper shell 28 and lower shell 26 are connected to each other at the contact edge 54 by laser welding. In this way, the spatula blade 22 has a very smooth and uniform contact edge 54, which is leaktight all the way round and easy to clean and on which no bacteria can settle.

Alternatively, the connection of the upper shell 28 and lower shell 26 can also be obtained by gluing of the superposed surfaces of the second portions 32 and 40 and of the third portions 34 and 42 or by soldering at the contact edge 54. The latter alternative may possibly require brief reworking in order to smooth the joins.

In this illustrative embodiment, the lower shell 26 (FIG. 3) and the upper shell 28 (FIG. 4) have each been produced from a workpiece by hydroforming. Therefore, the second and third portions 32 and 34 and the first portion 30 of the lower shell 26, and the second and third portions 40 and 42 and the first portion 38 and side wall 46 of the upper shell 28, in each case form a continuous closed surface.

Because of the hydroforming, this surface is in each case smooth and free of the irregularities that may occur in other methods of production of the shells.

When this method is used, the outlet opening 48 in the end wall 46 is formed later, e.g. by drilling, by punching or by laser cutting.

The proximal end (not shown here) of the cavity 52 can be closed, for example, by a retrofitted plate or, for example, by a surface formed integrally like the end wall 46 in the upper shell 28 or the lower shell 26. By closing the connection point between this plate or surface and the upper shell 28 and/or lower shell 26, for example by laser welding, a completely sealed cavity 52 is created, which allows the laryngoscope spatula 20 to be cleaned also with steam. An opening (not shown) can be formed in the proximal wall of the cavity for passage of the light guide 24 and/or of the abovementioned electrical leads into the head 14 and into the handle 12.

In the illustrative embodiment shown here, the spatula blade 22 has a rounded spatula tip 66 at the distal end (FIG. 1 and FIG. 2). This is attached by welding or also by soldering or gluing.

In the method for producing the spatula blade 22 of the laryngoscope spatula 20, the upper shell 28 and the lower shell 26 are first of all each formed from a corresponding metal blank by hydroforming.

The first portion 30, the second portion 32 and the third portion 34 of the lower shell 26 are formed. Similarly, the first portion 38, the second portion 40, the third portion 42 and the end wall 46 of the upper shell 28 are formed.

The second portions 32 and 40 and the third portions 34 and 42 thus formed are then laid flat on each other, the light guide 24 having first been secured on the likewise previously drilled outlet opening 48 and being arranged in the resulting cavity 52.

The lower shell 26 and the upper shell 28 are connected to each other by laser welding at the contact edge 54 formed by the edge 36 of the lower shell 26 and by the edge 50 of the upper shell 28.

The rounded spatula tip 66 is then placed on the distal end of the spatula blade 22 and connected to the spatula blade 22 by subsequent welding.

Brief reworking of these weld seams may also be carried out at this location in order to create smooth, easy-to-clean transitions between spatula blade 22 and spatula tip 66.

Alternatively, the spatula tip 66 is already formed in the distal end of the shells 26 and 28 in the forming step, i.e. during production of the upper shell 28 and lower shell 26 by hydroforming. It can either be present in the form of one of the two shells 26 or 28 or can be formed as respective parts in both shells 26 and 28. As in the cases described above, subsequent laser welding around the edge then provides a spatula blade that has smooth transitions and no irregularities and therefore does not require any reworking and is easy to clean.

In this way, the laryngoscope spatula 20 is produced which is completely smooth at the surfaces, because of the hydroforming, and at the contact edge 54, because of the laser welding, and is easy to clean.

What is claimed is:

1. A laryngoscope spatula, comprising: a spatula blade having a length in a longitudinal direction, said spatula blade having: an upper shell having, in cross-section transverse to said longitudinal direction, a first upper shell portion, a second upper shell portion and a third upper shell portion, said second upper shell portion and said third upper shell portion being mutually oppositely directed away from said first upper shell portion such that said upper shell has a substantially Z-shape configuration, a lower shell having, in cross-section transverse to said longitudinal direction, a first lower shell portion, a second lower shell portion and a third lower shell portion, said second lower shell portion and said third lower shell portion being mutually oppositely directed away from said first lower shell portion such that said lower shell has a substantially Z-shape configuration, said first upper shell portion forming a first side wall and said first lower shell portion forming a second side wall spaced apart from said first side wall along at least part of said length of said spatula blade, said second upper shell portion and said second lower shell portion partially lying flat on each other and forming a first limb extending from said first side wall to beyond said second side wall, said third upper shell portion and said third lower shell portion partially lying flat on each other and forming a second limb extending from said second side wall to beyond said first side wall, said first and second side walls and said first and second limbs forming a cavity; wherein the upper shell and lower shell are separate pieces prior to being attached to one another to form the spatula blade.

2. The laryngoscope spatula of claim 1, wherein said cavity has a distal end, and wherein said cavity is closed off at said distal end by an end wall that extends transversely with respect to said longitudinal direction of said spatula blade, and wherein said end wall is designed in one piece with said first upper shell portion and said second upper shell portion of said upper shell.

3. The laryngoscope spatula of claim 2, wherein said upper shell is produced by a forming method, in which said first upper shell portion is formed in one piece with said second upper shell portion and said third upper shell portion and with said end wall.

4. The laryngoscope spatula of claim 1, wherein said lower shell is produced by a forming method, in which said first lower shell portion is formed in one piece with said second lower shell portion and said third lower shell portion of said lower shell.

5. The laryngoscope spatula of claim 1, wherein at least one of said lower shell and said upper shell is produced by hydroforming.

6. The laryngoscope spatula of claim 1, wherein said upper shell and said lower shell are glued to each other via said superposed second upper and lower shell portions and third upper and lower shell portions.

7. The laryngoscope spatula of claim 1, wherein said upper shell and said lower shell are soldered onto each other along a peripheral contact edge formed by mutually adjoining edges of said second upper and lower shell portions and third upper and lower shell portions.

8. The laryngoscope spatula of claim 1, wherein said upper shell and said lower shell are welded onto each other along a peripheral contact edge formed by mutually adjoining edges of said second upper and lower shell portions and said third upper and lower shell portions.

9. The laryngoscope spatula of claim 8, wherein said upper shell and said lower shell are welded onto each other along said peripheral contact edge by laser welding.

10. The laryngoscope spatula of claim 1, wherein said spatula blade has a rounded spatula tip at a distal end of said spatula blade.

11. The laryngoscope spatula of claim 10, wherein said spatula tip is connected to said spatula blade by at least one of welding, soldering, gluing.

12. The laryngoscope spatula of claim 10, wherein said spatula tip is formed in one piece with at least one of said upper shell and said lower shell.

13. A method for producing a spatula blade of a laryngoscope spatula, comprising the steps of: providing an upper shell and a lower shell, wherein said upper shell, in cross-section transverse to a longitudinal direction, has a first upper shell portion, a second upper shell portion and a third upper shell portion, said second upper shell portion and said third upper shell portion being mutually oppositely directed away from said first upper shell portion such that said upper shell has a substantially Z-shape configuration; said lower shell having, in cross-section transverse to said longitudinal direction, a first lower shell portion, a second lower shell portion and a third lower shell portion, said second lower shell portion and said third lower shell portion being mutually oppositely directed away from said first lower shell portion such that said lower shell has a substantially Z-shape configuration; laying said second upper shell portion flat on said second lower shell portion, and laying said third upper shell portion flat on said third lower shell portion; firmly connecting said upper shell and said lower shell to each other by joining said second upper and lower shell portions and said third upper shell and lower shell portions such that said second upper and lower shell portions form a first limb and said third upper and lower shell portions form a second limb, and said first upper shell portion forms a first side wall and said first lower shell portion forms a second side wall, as a result of which a cavity is formed along at least part of a length of said spatula blade.

14. The method of claim 13, further comprising closing off a distal end of said cavity by an end wall which extends transversely with respect to a longitudinal direction of said spatula blade and which is produced in one piece with said first upper shell portion and said second upper shell portion.

15. The method of claim 13, wherein said step of providing said lower shell comprises producing said lower shell by a forming method, in which said first portion is formed in one piece with said second lower shell portion and said third lower shell portion.

16. The method of claim 13, wherein said step of providing said upper shell comprises producing said upper shell by a forming method, in which said first upper shell portion is formed in one piece with said second and said third upper shell portion and with said end wall of said upper shell.

17. The method of claim 13, wherein said step of providing said upper shell and said lower shell comprises producing at least one of said lower shell and said upper shell by hydroforming.

18. The method of claim 13, wherein said step of firmly connecting said upper shell and said lower shell to each other comprises gluing said upper shell and said lower shell to each other via said superposed second upper and lower shell portions and third upper and lower shell portions.

19. The method of claim 13, wherein said step of firmly connecting said upper shell and said lower shell to each other comprises soldering said upper shell and said lower shell onto each other along a peripheral contact edge formed by mutually adjoining edges of said second upper and lower shell portions and third upper and lower shell portions.

20. The method of claim 13, wherein said step of firmly connecting said upper shell and said lower shell to each other comprises welding said upper shell and said lower shell onto each other along a peripheral contact edge formed by mutually adjoining edges of said second upper and lower shell portions and said third upper and lower shell portions.

21. The method of claim 20, wherein said step of welding comprises laser welding.

22. The method of claim 13, further comprising connecting a rounded spatula tip onto a distal end of said spatula blade, wherein said step of connecting comprises at least one of welding, soldering, gluing.

23. The method of claim 13, wherein said step of providing said upper shell and said lower shell further comprises providing at least one of said upper shell and said lower shell having a spatula tip arranged at a distal end of said spatula blade which is formed in one piece with said at least one of said upper shall and said lower shell.

* * * * *